(12) United States Patent
Foquet et al.

(10) Patent No.: US 7,907,800 B2
(45) Date of Patent: * Mar. 15, 2011

(54) METHODS FOR MONITORING REACTIONS IN ZERO MODE WAVEGUIDES

(75) Inventors: Mathieu Foquet, Redwood City, CA (US); Paul Peluso, San Carlos, CA (US); Stephen Turner, Menlo Park, CA (US); Daniel Bernardo Roitman, Menlo Park, CA (US); Geoffrey Otto, San Carlos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 175 days.

This patent is subject to a terminal disclaimer.

(21) Appl. No.: 12/341,556

(22) Filed: Dec. 22, 2008

(65) Prior Publication Data

US 2009/0325166 A1    Dec. 31, 2009

Related U.S. Application Data

(63) Continuation of application No. 11/761,251, filed on Jun. 11, 2007, now Pat. No. 7,486,865.

(60) Provisional application No. 60/812,863, filed on Jun. 12, 2006.

(51) Int. Cl.
*G02B 6/00*    (2006.01)

(52) U.S. Cl. ............ 385/12; 385/129; 385/130; 385/131
(58) Field of Classification Search .................... 385/12, 385/129, 130, 131
See application file for complete search history.

(56) References Cited

U.S. PATENT DOCUMENTS

| | | | |
|---|---|---|---|
| 5,624,711 A | 4/1997 | Sundberg et al. | |
| 5,919,523 A | 7/1999 | Sundberg et al. | |
| 5,976,336 A | 11/1999 | Dubrow et al. | |
| 6,261,776 B1 | 7/2001 | Pirrug et al. | |
| 6,917,726 B2 | 7/2005 | Levene et al. | |
| 7,013,054 B2 | 3/2006 | Levene et al. | |
| 7,181,122 B1 | 2/2007 | Levene et al. | |
| 7,292,742 B2 | 11/2007 | Levene et al. | |
| 7,486,865 B2 * | 2/2009 | Foquet et al. ............ | 385/129 |

OTHER PUBLICATIONS

Miyake et al. (2008) "Real-Time Imaging of Single-Molecule Fluorescence with a Zero-Mode Waveguide for the Analysis of Protein-Protein Interaction." Anal. Chem., 80(15): 6018-6022.

* cited by examiner

*Primary Examiner* — Jennifer Doan
(74) *Attorney, Agent, or Firm* — Robert H. Reamey

(57) ABSTRACT

Methods for monitoring reactions are provided, including methods involving monitoring reactions in zero mode waveguide substrates. The zero mode waveguide substrates have zero mode waveguides wherein the core extends through the cladding layer at least partially into the transparent substrate.

20 Claims, 6 Drawing Sheets

METHODS FOR MONITORING REACTIONS IN ZERO MODE WAVEGUIDES

CROSS-REFERENCE TO RELATED APPLICATIONS

This application claims the benefit under 35 U.S.C. §119 (e) of U.S. Ser. No. 60/812,863, filed Jun. 12, 2006, which is hereby expressly incorporated by reference in its entirety.

STATEMENT REGARDING FEDERALLY SPONSORED RESEARCH

Portions of the invention were made with government support under NHGRI Grant No. R01-HG003710-01 and the government has certain rights to the invention.

BACKGROUND OF THE INVENTION

The application of widely differing scientific disciplines to biological research has yielded profound advances in the ways that biological systems are characterized and monitored, and the way in which biological disorders are treated. In particular, the combination of solid state electronics technologies to biological research applications has provided a number of important advances including, e.g., molecular array technology, i.e., DNA arrays (See, U.S. Pat. No. 6,261,776), microfluidic chip technologies (See, U.S. Pat. No. 5,976,336), chemically sensitive field effect transistors (ChemFETs), and other valuable sensor technologies.

Zero mode waveguide (ZMW) technology provides yet another extension of these semiconductor fabrication technologies to different areas of research and diagnostics. In particular, ZMW arrays have been applied in a range of biochemical analyses and particularly in the field of genetic analysis. ZMWs typically comprise a nanoscale core, well or opening disposed in an opaque cladding layer that is disposed upon a transparent substrate. Due to the narrow dimensions of the core electromagnetic radiation that is of a frequency above a particular cut-off frequency will be prevented from propagating all the way through the core. Notwithstanding the foregoing, the radiation will penetrate a limited distance into the core, providing a very small illuminated volume within the core. By illuminating a very small volume, one can potentially interrogate very small quantities of reagents, including, e.g., single molecule reactions.

By monitoring reactions at the single molecule level, one can precisely identify and/or monitor a given reaction. This is the basis behind a particularly promising field of single molecule DNA sequencing technology that monitors the molecule by molecule synthesis of a DNA strand in a template dependant fashion by a single polymerase enzyme.

Despite the foregoing advances, a number of additional improvements and advances are available. The present invention provides a number of such advances and improvements.

BRIEF SUMMARY OF THE INVENTION

The present invention is generally directed to improvements in the configuration and/or manufacturing of substrates used in chemical and biochemical analyses, and particularly to substrates having optical features fabricated into such substrates, such as zero mode waveguides (ZMWs).

In a first aspect, the invention provides a zero mode waveguide substrate that comprises a transparent substrate layer having at least a first surface, a metal cladding layer disposed upon the first surface of the transparent substrate layer and an aperture disposed through the cladding layer to the transparent substrate layer, and forming a core region surrounded by the metal cladding layer, wherein the core is dimensioned to prevent electromagnetic radiation of a frequency greater than a cut-off frequency from propagating entirely through the core. The substrate also includes a sacrificial anode disposed upon the cladding layer.

Relatedly, the invention provides methods of monitoring a reaction, comprising providing a reaction mixture within a core of a zero mode waveguide that comprises a metal cladding layer, wherein the zero mode waveguide includes a sacrificial anode, and monitoring the reaction mixture within an illumination volume of the core.

In an additional aspect, the invention provides a zero mode waveguide substrate that comprises a transparent substrate layer, an opaque cladding layer, and a core, comprising an aperture disposed through the cladding layer and extending at least partially into the transparent substrate layer.

DETAILED DESCRIPTION OF THE INVENTION

Figure 1:
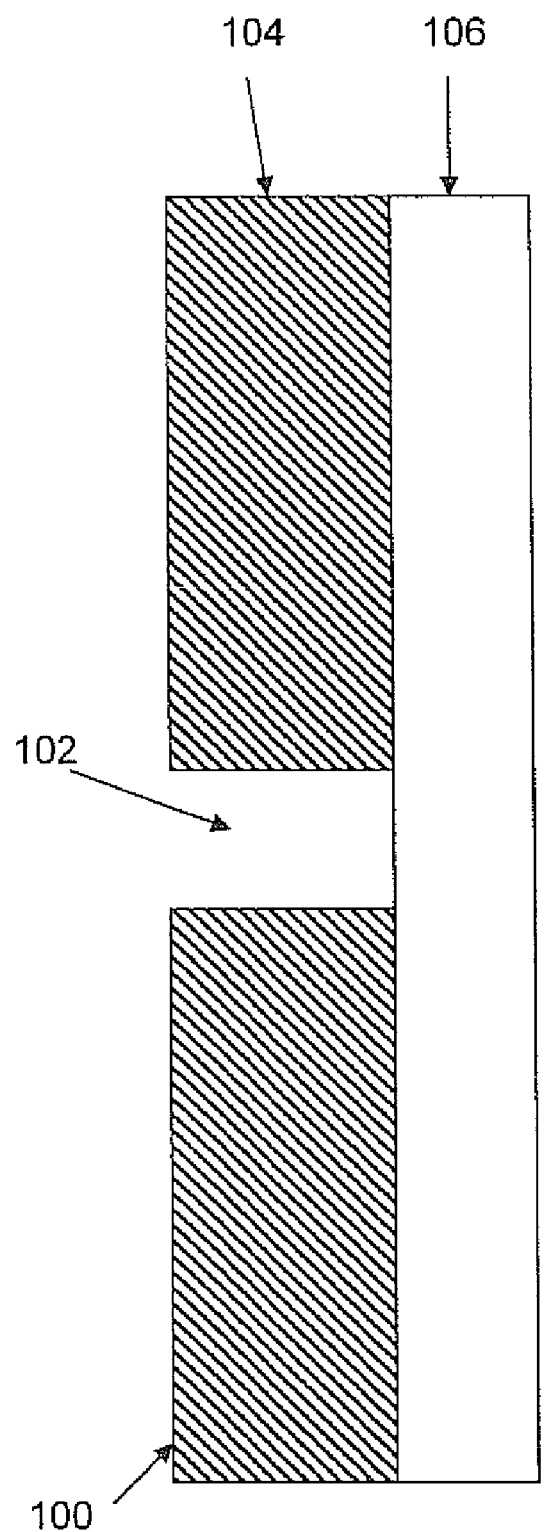
FIG. 1 provides a schematic illustration of a Zero Mode Waveguide (ZMW) disposed in a substrate.

The present invention is generally directed to improvements in the configuration and/or manufacturing of substrates used in chemical and biochemical analyses, and particularly to substrates having optical features fabricated into such substrates, such as zero mode waveguides (ZMWs).

In the context of the present invention, analytical substrates generally comprise a rigid or semi-rigid solid substrate, typically substantially planar in overall configuration, upon which reactions of interest may be carried out and monitored, using an associated detection system, such as a fluorescence microscope, optical imaging system, or electrical signal detection system. Typically, such substrates may have additional functional components manufactured into the substrate or disposed upon a surface of the substrate. Such components include, e.g., molecular components, such as molecular binding moieties, e.g., antibodies, nucleic acids non-specific chemical coupling groups, binding peptides, or the like, or property altering groups such as hydrophobic or hydrophilic groups, to provide areas of relative hydrophobicity or hydrophilicity on the substrates. Likewise, the substrates may have structural components fabricated onto or into the substrates, including, e.g., barriers, wells, posts, pillars, channels, troughs, electrical contacts, mask layers, cladding layers or the like.

The present invention may be generally applied across a range of different substrate types, depending upon the need for the particular solution offered by the invention. For example, in a first aspect, the invention provides substrates that include arrays of zero mode waveguides (ZMWs) disposed therein. ZMWs are typically characterized by a cladding component that surrounds a core component, where the core is dimensioned such that electromagnetic energy entering the core that is of a frequency that falls below a particular threshold or cut-off frequency, is precluded from propagating entirely through the core. The result is that direction of such electromagnetic energy at the core results in a very small region of illumination within only a portion of the core. Where the core is provided as an open volume bounded by the cladding, the result is an ability to illuminate an extremely small volume within the core. The ability to illuminate extremely small volumes, e.g., of chemical or biochemical reactants, is of particular value in a number of applications. These ZMW arrays, their fabrication and use, are described in U.S. Pat. No. 6,917,726, which is incorporated herein in its entirety for all purposes.

Zero mode waveguides typically comprise cross-sectional dimensions of from about 10 nm to about 250 nm, and are preferably between about 20 and about 100 nm in cross sectional dimension. The ZMWs are typically circular in cross-section, although they may also be elongated structures, e.g., ovals, ellipses, slits, grooves, or other non-circular shapes. The depth of the core of the zero mode waveguide, subject to the discussion herein, is typically defined, at least in part, by the thickness of the cladding layer, which will typically range from about 25 nm to about 500 nm thick, and preferably, between about 50 nm and about 200 nm thick. One may select a desired depth from the full range of applicable depths, depending upon the desired application.

The zero mode waveguides of the invention are typically fabricated into a substrate that includes a transparent substrate layer and an opaque cladding layer deposited upon the transparent substrate. The core portion of the waveguides comprises an aperture disposed through the cladding layer to the transparent layer to define a well having an open upper end and a lower end that is capped by the transparent substrate. A schematic illustration of such waveguides is shown in FIG. 1. As shown, the overall substrate 100 includes a waveguide core 102 disposed within opaque cladding layer 104 and continuing through to the transparent substrate layer 106.

ZMW fabrication can be carried out by a number of methods. However in preferred aspects, a layered fabrication strategy is used that provides a thin metal film over a transparent planar substrate, e.g., glass, fused silica, quartz, alumina, transparent polymers, or the like. Defining the cores is usually carried out by providing an appropriate resist layer over the transparent substrate and developing the resist layer to yield pillars or posts as a negative image of the desired waveguide cores. An opaque film, such as a thin metal film or semiconductor film layer, is then deposited over the substrate to provide the cladding layer, and the resist pillars are removed to yield apertures or cores, in their place, surrounded by the cladding layer. Typical metal cladding layers include any of a number of metal films that may be processed using conventional metal deposition techniques, such as sputtering and/or evaporation. Such metals include aluminum, gold, platinum, chromium, and the like as well as combinations of these, e.g., as multilayer depositions. Semiconductor cladding layers are also useful in a variety of applications and include, e.g., any of a variety of Group III-V, IV, and/or II-VI semiconductors that may be deposited upon the substrate using, e.g., vapor deposition.

Defining the resist pillars may be carried out by a variety of methods known in the art of semiconductor processing, including, e.g., photolithographic methods, e-beam lithography techniques, nano-imprint lithography, or the like.

In at least a first aspect, the overall structure of the zero mode waveguide may incorporate additional functionality that, in preferred cases, is applied as additional layers to the overall substrate.

As noted above, preferred zero mode waveguides comprise metal cladding layers disposed over transparent substrate materials. In the application of such metallized substrates to chemical and/or biochemical operations, they will inevitably be exposed to environments that can be somewhat damaging to the metal, including, e.g., relatively high salt concentrations and/or non-neutral pH environments, e.g., acidic or basic conditions. All of these factors add to the tendency for such materials to be susceptible to corrosion. In particular, exposure of these metallic components to high salt environments can create an opportunity for galvanic corrosion to occur. Accordingly, in at least one aspect, the present invention provides a zero mode waveguide substrate that includes a sacrificial or galvanic anode as a component of the substrate. Such galvanic anodes may be integral to the substrate, e.g., deposited as integral to or as a discrete layer upon a substrate, or they may be added as a separate component to the reaction mixture, e.g., as particles, strips or wires. Any of a variety of different metals can be employed as the galvanic anode, including, e.g., zinc, magnesium, aluminum, iron, nickel or any other metal that functions as a sacrificial anode for the underlying cladding layer metal. It will be appreciated that selection of an optimized metal anode layers may depend to some extent upon the make-up of the underlying cladding layer. Additionally, because the environment to which a device is exposed will vary according to the needs of an application, the reduction potentials of metals will vary from their standard values. As such, numerous materials can be used as a sacrificial anode. For a cladding material with a half-cell potential X (under the conditions used), and an anode materials with a half-cell potential Y, a metal can be used as a sacrificial anode if Y is less than X. In some cases, either the cladding material or the anode material or both will spontaneously undergo a chance to another surface state with new half cell potentials X' and Y', and if Y' is less than X' then these materials are usable as sacrificial anodes. Preferred materials in the capacity of sacrificial anode materials include: Magnesium, Zinc. Beryllium, Cadmium, Uranium, Aluminum, Indium, Tin, Lead, Iron, Nickel, Copper, Chromium, tantalum, and tungsten. In particularly preferred aspects, a zinc layer is deposited along with or on top of the metal cladding layer. A variety of metal film deposition techniques may be employed to provide the anode layer over the cladding layer, including sputtering, evaporation, plasma vapor deposition, and the like.

In a related embodiment, the additional layer may be electrically insulated from the cladding layer via a nonconductive layer disposed between the anode layer and the cladding layer. In this embodiment, an electrical potential can be applied directly to the anode layer, thus removing the restriction that the anode material have a particular reduction potential. In this embodiment, the invention provides an electrical contact to the cladding layer, and a separate electrical contact to the anode layer. The nonconductive layer can be applied in a separate step, or it can be a native oxide of one of the other materials to be applied. For example, the native oxide of aluminum is non-conductive, and methods are known in the art for forming an insulating layer of aluminum oxide on a conductive aluminum layer.

Figure 2:
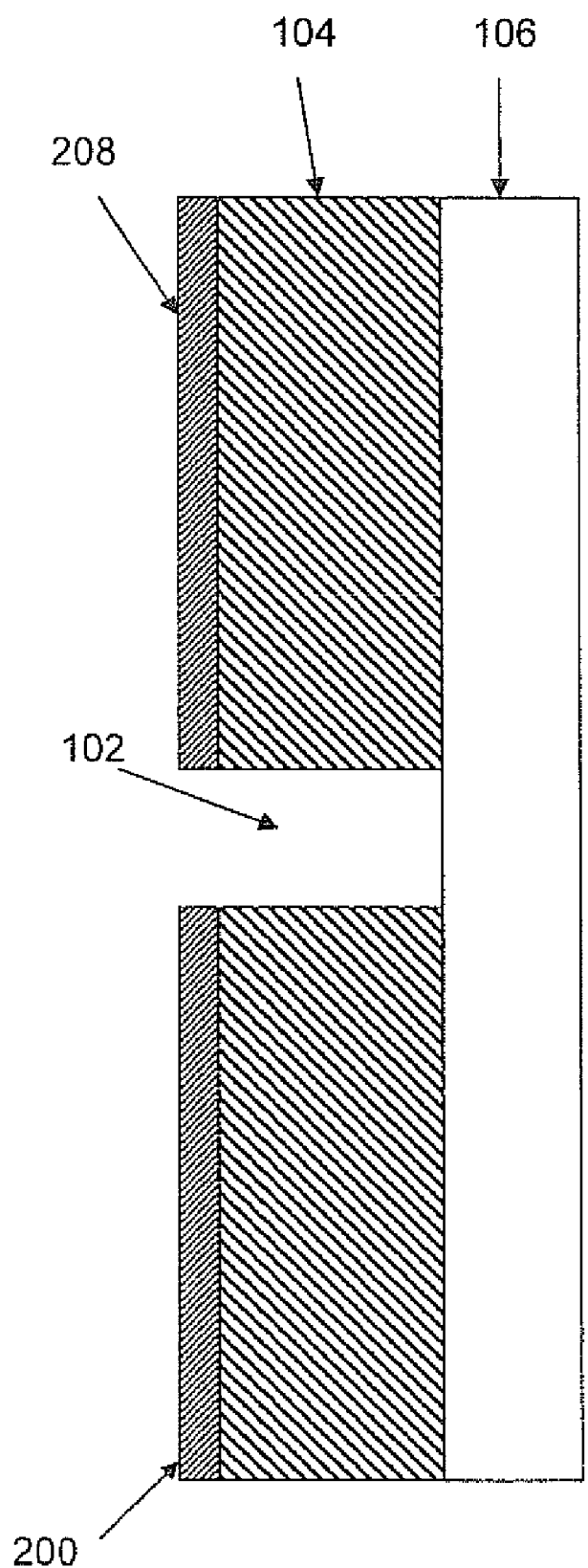
FIG. 2 provides a schematic illustration of a ZMW including a sacrificial anode layer.

In the context of the manufacturing processes set forth above, the zinc layer may generally be co-deposited with the metal cladding layer or deposited as a subsequent layer on top of the metal cladding layer. Once the resist pillars are removed, the waveguide core would be disposed through both the galvanic anode and metal cladding layers. Typically the anode layer will be from about 0.1 nm to about 100 nm thick, preferably from about 1 to about 100 nm thick, from about 1 to about 50 nm thick and in some cases from about 10 to about 50 nm thick. An example of a waveguide substrate in accordance with this aspect of the invention is shown in FIG. 2. As shown, and with reference to FIG. 1, the overall ZMW device 200 again includes a core 102 disposed in cladding layer 104 that is, in turn, disposed on the surface of transparent substrate 106. In addition to the foregoing, however, a sacrificial anode layer 208 is disposed upon the upper surface of the cladding layer 104, and serves to prevent excessive galvanic corrosion of the metal cladding layer during application.

In alternative aspects, a discrete anode component may be added to the waveguide array in other than a standard deposition process. In particular, an appropriate metal particle, strip or the like may be deposited upon the waveguide array, provided it is of sufficient size, e.g., sufficiently large or sufficiently small, that it does not interfere with the waveguide functions, e.g., blocking the openings of excessive numbers of the cores.

Figure 3:
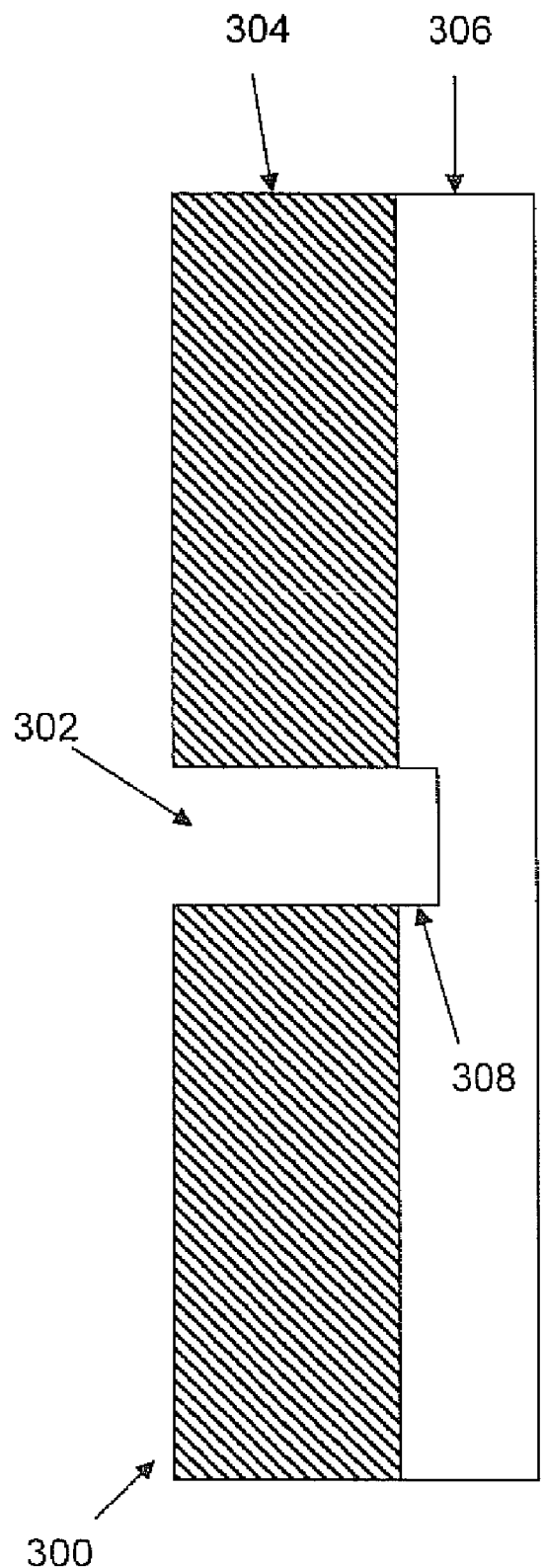
FIG. 3 provides a schematic illustration of a ZMW including an increased volume region within the transparent substrate layer.

In another alternate structural configuration, the zero mode waveguides are provided with a space or volume at the end of the core that extends beyond the cladding layer into the transparent substrate. In particular, by providing an additional extension of the volume created by the core, one can obtain a number of advantages over a zero mode waveguide where the volume and core are co-extensive, e.g., as in FIG. 1. An example of a waveguide having this alternative structure is illustrated in FIG. 3. As shown, a zero mode waveguide substrate 300 includes a core 302 disposed through a cladding layer 304, that is deposited upon a transparent substrate 306. The waveguide structure also includes a recess 308, well or extension of the core volume into the transparent substrate 306 to increase the volume of the overall waveguide structure. In particular, in the case of ZMWs that include modified surfaces, e.g., having engineered surfaces that include reactive molecules and/or linker molecules and/or protective surface treatments, i.e., to prevent nonspecific surface associations, the resulting active surface may be moved further away from the underlying substrate surface. As a result, the reactions of interest, e.g., being carried out at the reactive surface, may fall at the edges or outside of the optimal observation volume of a ZMW. As such, by recessing the underlying substrate surface, one can better position a reactive surface within the observation volume. This benefit is schematically illustrated in FIG. 6.

Figure 6:
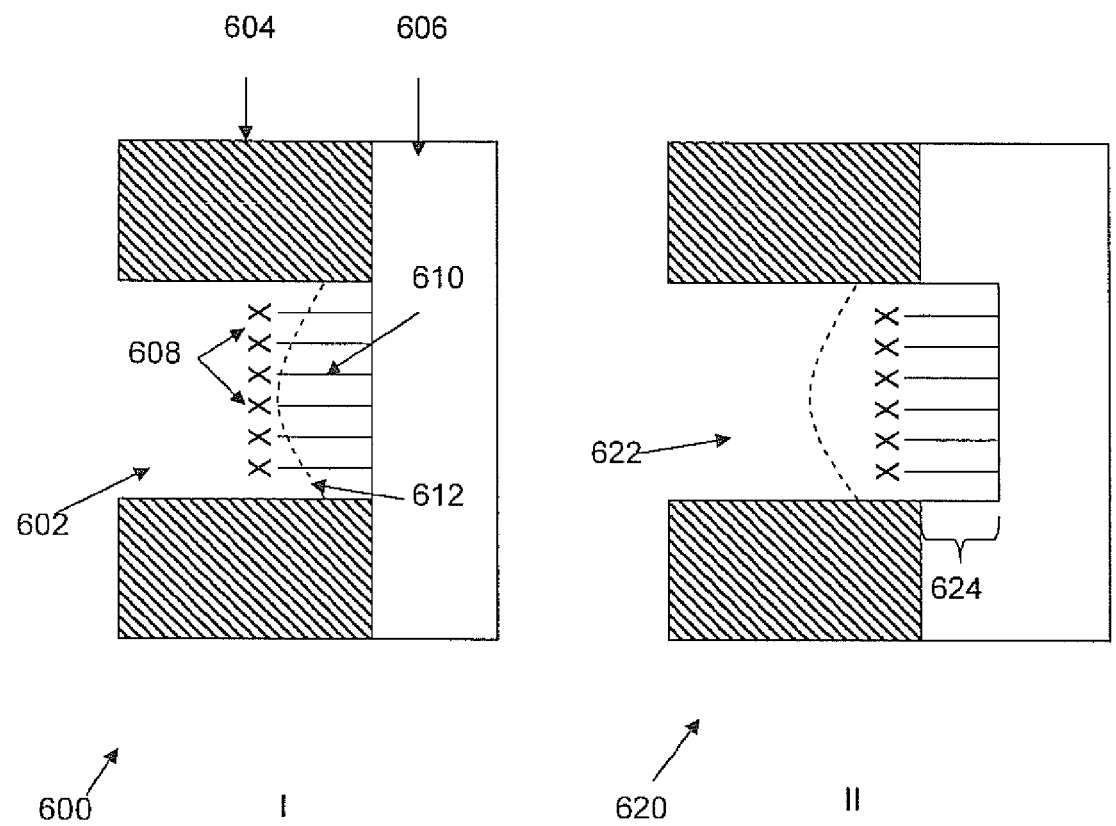
FIG. 6 is a schematic illustration of the comparative benefits of ZMWs including recessed surfaces.

In a non-recessed ZMW, as illustrated in Panel I of FIG. 6. As shown, a ZMW substrate 600 includes a core 602 disposed within a cladding layer 604 through to the transparent substrate layer 606. A reactive surface as indicated by Xs 608, e.g., for performing a desired reaction of interest such as a nucleic acid polymerization reaction, is provided within a ZNMW core 602, and is coupled to the underlying substrate 606 surface via linker molecules 610. Because of the size of the linkers 610, and potentially other surface modifications, the reactive surface 608 may be disposed at the edge or outside of the observation volume (shown bounded by dashed line 612). By recessing the lower surface of the underlying substrate, however, one can alleviate this potential issue. In particular, as shown in FIG. 6, panel II, the ZMW 620 includes a recessed lower surface 624 at the base of the core 622 that results in reactive surface 608 falling well within the observation volume. This provides a zero mode waveguide having, inter alia, a more readily tunable observation volume, e.g., adjustable beyond the thickness of the cladding layer alone, higher signal level for optics disposed below the waveguides, resulting in improved signal to noise ratios.

In addition to the aforementioned advantages, the increase in the volume of the detection region provides an advantage in the statistics of occupancy of molecules of interest in a detection volume. In some instances it is desirable for an assay to have one and only one molecule under observation in each confinement. In the case where the bottom of the cladding and the floor of the device are in the same place, the confinement has a profile that is exponentially decreasing with a short attenuation length. The result is that it is rare that a molecule will be positioned in the detection zone and that a second molecule will not be present higher up in the detection zone such that it creates background noise to the first molecule. By lowering the floor, the profile changes to emulate a step function, where there is a portion of the device that is "in" the detection zone with relatively uniform observation efficiency, and another part of the device that is "out" of the detection volume with the very fast exponential decay separating the two regions. In this latter situation the probability of obtaining by random chance the arrangement that there is one molecule in the detection zone and no molecules in the exponential decay region is greatly increased. An additional advantage of the relative uniformity provided by the deep well is that the level of fluorescence output of a single molecule is made less dependent on position, and therefore more uniform in time when there is some freedom for fluctuation due to a flexible linker tethering the fluorophore to the device.

The recess or well 308 at the transparent substrate 306 is typically of comparable cross sectional dimensions as the core, e.g., diameter, but may vary in its depth depending upon the desired application and functionality.

Fabrication of the modified zero mode waveguides according to this aspect of the invention may be carried out by a number of methods. For example, in a first preferred aspect, the well is fabricated as an additional deposition step in the process of ZMW fabrication, that takes place prior to deposition of the metal cladding layer. In particular, using the negative image of the resist pillars, a layer of transparent material, e.g., of the same or similar composition to the underlying transparent substrate, is deposited over the transparent substrate. The metal cladding layer, and optionally, any additional layers, such as a galvanic anode layer, is then deposited over it. Once the pillars are removed from the structure, a waveguide core is left in the cladding layer with an additional volume that extends into the transparent substrate layer. This process is schematically illustrated in FIG. 4.

Figure 4:
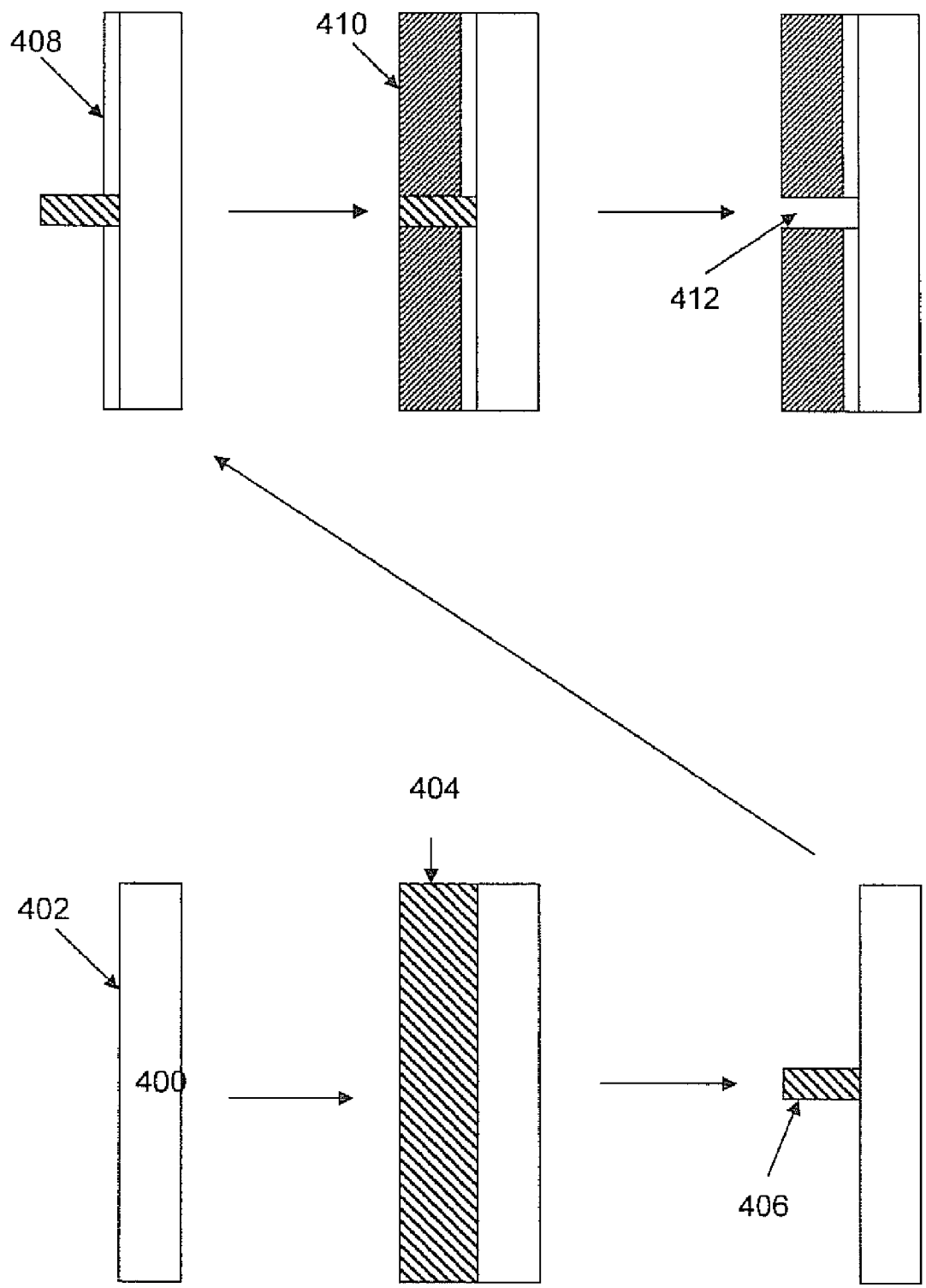
FIG. 4 provides a schematic exemplary fabrication process for the ZMW shown in FIG. 3.

As shown in FIG. 4, a transparent substrate 400 is provided having an upper surface 402. A resist layer 404 is then deposited over the surface 402. The resist is exposed and developed to yield a negative image of the desired waveguide cores, shown as pillars 406. A layer of additional transparent material 408 is then deposited upon the exposed surface 402 of the substrate to build up the transparent substrate layer around the pillar 406. The transparent material is preferably the same or similar in composition to the underlying transparent substrate 400. For example, in the case of glass substrates, an $SiO_2$ layer may be deposited over the substrate surface using any of a variety of techniques known in the field of semiconductor manufacturing, including, e.g., use of spin on glass, plasma enhanced chemical vapor deposition, vapor deposition of silicon followed by oxidation to $SiO_2$ (e.g., thermal oxidation). A metal cladding layer 410 is then deposited over the transparent layer 408. The resist pillars are then removed from the overall substrate using, e.g., a lift-off or "knock-off" process, yielding the open core 412 of the waveguide structures disposed in the cladding layer. Additionally, the core volume extends into the additional transparent layer 408, to provide added volume to the core.

In an alternative process, the waveguide core may be used as a masking layer for an additional etching step. In particular, a ZMW is fabricated using the processes set forth above. The metal cladding layer then functions as a masking layer for a subsequent etching step. In this context, the etchant used and the amount of etch time are selected so as to yield a desired geometry of the etched space. For example, where a substrate is etched using anisotropic reactive ion etching (RIE), the resulting feature will have vertical side walls and the same aerial view as the opening in the cladding. In this instance, methods are known in the art for etching the substrate material with a tolerable degree of selectivity to the cladding material. In the event that etching occurs isotropically (either using wet chemical etching or RIE), the time may be controlled to avoid yielding an etched volume that is substantially larger than the waveguide dimensions. Alternatively or additionally, one may use more crystalline substrates, e.g., quartz, or the like, where etching is more anisotropic despite the etching conditions, yielding a more confined etched space. Alternatively, dry etching techniques may be used. A schematic illustration of this process is shown in FIG. 5.

Figure 5:
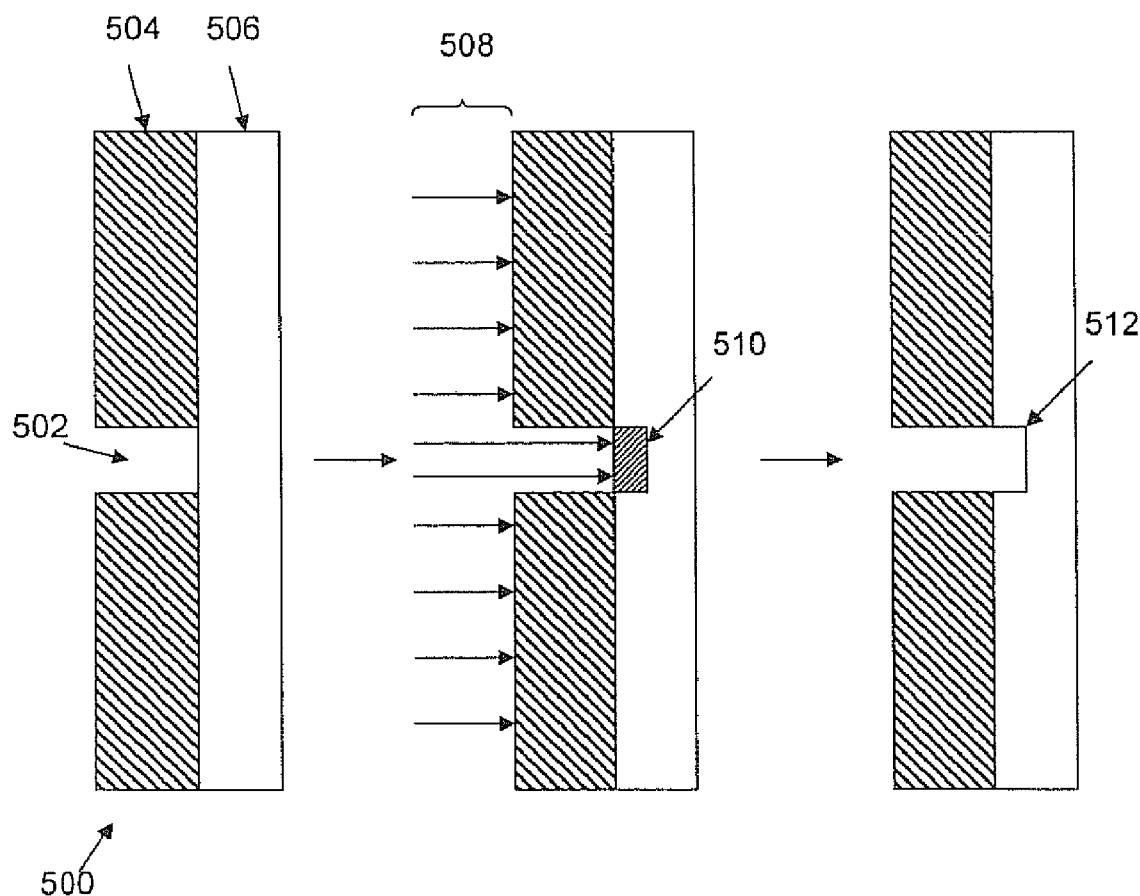
FIG. 5 shows an alternative exemplary fabrication process for producing the ZMW shown in FIG. 3.

As shown in FIG. 5, a ZMW substrate 500 includes a ZMW core 502 disposed through a metal cladding layer 504 disposed upon the transparent substrate 506, which in this aspect of the invention comprises an inorganic material, e.g., glass, quartz or fused silica. In accordance with this aspect of the invention, the cladding layer doubles as a masking layer for a subsequent etching step. In particular, the substrate is exposed to an appropriate etchant (as indicated by arrows 508) which etches additional depth into the core volume, e.g., as shown by shaded region 508 and depression 510. In some cases, it may be desirable to utilize metals in the cladding layer that are more routinely employed in lithographic techniques, such as chromium, gold, or the like, as they may have greater tolerance of the harsher etching environments than other metals or may function better as masking materials, providing higher resolution features.

What is claimed is:

1. A method of monitoring a reaction, comprising: providing a reaction mixture within a core of a zero mode waveguide substrate that comprises a cladding layer and a transparent substrate layer wherein the core extends through the cladding layer and into the transparent substrate layer.

2. The method of claim 1 wherein the reaction comprises a single molecule reaction.

3. The method of claim 1 wherein the reaction comprises enzyme mediated nucleic acid polymerization.

4. The method of claim 1 wherein the monitoring of the reaction comprises single molecule DNA sequencing.

5. The method of claim 1 wherein a molecular binding moiety is disposed upon a surface of the transparent substrate layer.

6. The method of claim 5 wherein the molecular binding moiety comprises an antibody, a nucleic acid coupling group, a non-specific chemical coupling group, or a binding peptide.

7. The method of claim 1 wherein a portion of the core extending into the transparent substrate layer comprises a reactive surface.

8. The method of claim 7 wherein the reaction is carried out, at least partially, at the reactive surface.

9. The method of claim 1 wherein the core extends partly into the transparent substrate layer such that a base of the core is formed within the transparent layer.

10. The method of claim 9 wherein the base of the core comprises a reactive surface.

11. The method of claim 10 wherein the reactive surface comprises a polymerase enzyme.

12. The method of claim 1 wherein hydrophobic groups, hydrophilic groups, or both hydrophobic and hydrophilic groups are disposed upon the substrate to provide areas of relative hydrophobicity or hydrophilicity on the substrate.

13. The method of claim 1 wherein the portion of the core within the transparent substrate layer has substantially equivalent cross sectional dimensions to the portion of the core within the cladding layer.

14. The method of claim 1 wherein the cross-sectional dimensions of the core range from about 10 nm to about 250 nm.

15. The method of claim 1 wherein the transparent substrate layer comprises a member selected from: glass, quartz, fused silica, alumina, and a transparent polymer.

16. The method of claim 1 wherein the cladding layer comprises a metal that is a member selected from aluminum, gold, platinum, and chromium.

17. The method of claim 1 further comprising observing the reaction with a fluorescence microscope, an optical imaging system, or an electrical signal detection system.

18. The method of claim 1 wherein the zero mode waveguide substrate comprises an array of zero mode waveguides.

19. A method of monitoring a single molecule DNA sequencing reaction comprising: providing a reaction mixture within a core of a zero mode waveguide substrate wherein the zero mode waveguide substrate comprises a metal cladding layer and a transparent substrate layer, wherein the core extends into the transparent substrate layer.

20. A method of monitoring a reaction comprising: providing a reaction mixture within a core of a zero mode waveguide substrate, the zero mode waveguide having observation volume that is at least partially outside of the cladding layer alone.

* * * * *